United States Patent
De Miguel et al.

(10) Patent No.: US 10,493,005 B2
(45) Date of Patent: Dec. 3, 2019

(54) MICROCOMPLEX FOR USE IN PHOTOEPILATION PROCESS TO OBTAIN IT AND COMPOSITION CONTAINING IT

(71) Applicants: Fundació Institut de Ciències Fotòniques, Barcelona (ES); Institució Catalana de Recerca I Estudis Avançats, Barcelona (ES)

(72) Inventors: Ignacio De Miguel, Barcelona (ES); Romain Quidant, Barcelona (ES)

(73) Assignees: Fundació Institut de Ciències Fotòniques, Barcelona (ES); Institució Catalana de Recerca I Estudis Avançats, Barcelona (ES)

( * ) Notice: Subject to any disclaimer, the term of this patent is extended or adjusted under 35 U.S.C. 154(b) by 86 days.

(21) Appl. No.: 15/543,763

(22) PCT Filed: Jan. 14, 2015

(86) PCT No.: PCT/EP2015/050570
§ 371 (c)(1),
(2) Date: Jul. 14, 2017

(87) PCT Pub. No.: WO2016/112971
PCT Pub. Date: Jul. 21, 2016

(65) Prior Publication Data
US 2018/0021226 A1  Jan. 25, 2018

(51) Int. Cl.
*A61K 9/50* (2006.01)
*A61K 8/02* (2006.01)
(Continued)

(52) U.S. Cl.
CPC .............. *A61K 8/0245* (2013.01); *A61K 8/19* (2013.01); *A61K 8/25* (2013.01); *A61K 8/736* (2013.01);
(Continued)

(58) Field of Classification Search
CPC .......... A61N 5/0617; A61K 9/10; A61K 9/14; A61K 9/50; A61K 9/5084
(Continued)

(56) References Cited

U.S. PATENT DOCUMENTS 7,696,473 B2 * 4/2010 Quidant ................. G21K 1/006
                                                              250/251
10,058,500 B2 * 8/2018 Quidant ................... A61K 8/46

FOREIGN PATENT DOCUMENTS

WO   WO-2012/027728 A2   3/2012
WO   WO-2013079105 A1   6/2013

OTHER PUBLICATIONS

Lee et al. Facile Preparation of Highly-Scattering Metal Nanoparticle-Coated Polymer Microbeads and Their Surface Plasmon Resonance, J. Am. Chem. Soc. 2009, 131, 5048-5049. (Year: 2009).*
(Continued)

*Primary Examiner* — Hoa (Holly) Le
(74) *Attorney, Agent, or Firm* — Marshall, Gerstein & Borun LLP

(57) ABSTRACT

The present invention relates to a microcomplex containing a modified nanoparticle adsorbed on a host microparticle and to a process to obtain it. The microcomplex is particularly useful for photoepilation. The present invention also relates to a composition containing the microcomplex and to the method for enhanced photoepilation based on the microcomplexes.

13 Claims, 6 Drawing Sheets

(51) Int. Cl.
    *A61K 8/25*    (2006.01)
    *A61Q 9/04*    (2006.01)
    *A61K 8/73*    (2006.01)
    *A61K 8/19*    (2006.01)
    *A61B 18/20*   (2006.01)
    *A61B 18/00*   (2006.01)

(52) U.S. Cl.
    CPC .............. *A61Q 9/04* (2013.01); *A61B 18/203* (2013.01); *A61B 2018/00476* (2013.01); *A61K 2800/413* (2013.01); *A61K 2800/61* (2013.01); *A61K 2800/624* (2013.01); *A61K 2800/651* (2013.01); *A61K 2800/81* (2013.01)

(58) Field of Classification Search
    USPC .......................... 424/490, 493, 479; 606/3, 9
    See application file for complete search history.

(56) References Cited

OTHER PUBLICATIONS

Gong et al., In situ self-assembly synthesis of gold nanoparticle arrays on polystyrene microspheres and their surface plasmon resonance, Colloid Polym Sci (2013) 291:239-244, DOI 10.1007/s00396-012-2601-6. (Year: 2013).*

Zhao et al., Iron-oxide nanoparticles embedded silica microsphere resonator exhibiting broadband all-optical wavelength tunability, Optics Letters, Jul. 1, 2014 / vol. 39, No. 13. (Year: 2014).*

International Search Report and Written Opinion issued in PCT/EP2015/050570, dated Nov. 17, 2015.

* cited by examiner

MICROCOMPLEX FOR USE IN PHOTOEPILATION PROCESS TO OBTAIN IT AND COMPOSITION CONTAINING IT

The present invention relates to a microcomplex containing a modified nanoparticle adsorbed on a host microparticle and to a process to obtain it. The microcomplex is particularly useful for photoepilation.

The present invention also relates to a composition containing the microcomplex and to the method for enhanced photoepilation based on the microcomplexes.

BACKGROUND ART

Photoepilation (also known as light hair removal) is a non-surgical cosmetic procedure that uses intense light to remove unwanted hairs and slow down their regeneration. Light hair removal (including laser and IPL-Intense Pulsed Light) is the fastest growing non-surgical esthetic application.

Current approaches rely on the natural color (absorption) contrast between the hair and the skin to damage the hair by photo heating. They consequently fail for clear hairs (blond and white) and, even in the ideal configuration of dark hairs on clear skin; the required light intensities are responsible for local skin injuries that can become permanent. The less cost and frequency of the treatment are the factors behind the growth of the market.

A method for enhanced photoepilation was described in the patent application WO2013079105 in which plasmonic gold nanocomplexes are used to artificially enhance the absorption contrast between the hair and the skin. In this method cationic gold nanocomplexes able to accumulate at the hair cuticle and root levels are used. Those nanocomplexes present a strong surface plasmon resonance (SPR) in the near infrared and thus can be heated up very efficiently at wavelengths out of the melanin absorption spectrum. However, in practice, only a finite number of nanocomplexes will reach the hair cuticle/root, thus limiting the actual depilation efficiency, because the quantity of heat generated at the hair cuticle/root is directly proportional to the quantity of delivered nanocomplexes. In addition nanocomplexes belong to nanotechnologies and from a commercial/societal viewpoint, they may raise some issues related to tiny size like potential toxicity or clearance.

Thus, from what is known in the art, it is derived that the increase the amount of nanocomplexes reaching the targeted region and lift the issues related to the nanosize of the nanocomplexes while maintaining the photothermal properties of individual plasmonic nanoparticles is of great interest.

SUMMARY OF THE INVENTION

Inventors have found a microcomplexes comprising a nanoparticle adsorbed on the surface of the microparticles with excellent properties for use in photoepilation. The microcomplexes increases the amount of nanocomplexes reaching the targeted region and lift the issues related to the nanosize of the nanocomplexes while maintaining the photothermal properties of individual nanoparticles.

The microcomplexes of the invention, due to their positive surface potential, show a strong interaction with the keratinized structures, for example hair cuticle or hair follicle cells responsible of the hair growth, because they all have global negative charge.

Also there is a substantial increase of the heating efficiency of the microcomplexes of the invention over the nanocomplexes.

The number of heating nanoparticles increases with the size of the host microparticle, consequently one would thus conclude that the heat delivery to the hair increases with the host particle size. However because the temperature increases in a short spatial range, nanoparticles that are too far apart from the hair surface would not significantly contribute to deliver heat. We discovered then that there is an optimum size for the host microparticle that is between 100-2000 nm diameter.

Also the heating efficiency of the microcomplex described in the invention is very surprising, because not all the nanoparticles adsorbed on the surface of the microparticles are in direct contact with the hair.

The nanoplarticles present in the microcomplex of the present invention are plasmonic nanoparticles. The plasmonic nanoparticles keep their resonant properties when attached to a solid support although the position of the resonance may slightly red shift because of the higher refractive index of the support. The spectral position of the Localized Surface Plasmon (LSP) resonances depends on constitutive material of the particle, its geometry and dielectric surrounding. In the present invention, the density of nanoparticles attached to the host microparticle is such that the SPR properties of the nanoparticles are mostly conserved (in other words the microcomplex keep nearly the same SPR properties as the isolated gold nanoparticles). In addition, the polycationic nature of the nanocomplexes is transferred to the microcomplexes in a way the microcomplexes efficiently adhere to the keratinized hair follicle structures. This leads to a very efficient method to accumulate nanocomplexes in the hair follicle and thus achieve enhanced heating capability upon illumination. This includes hair follicles on which hairs have been removed, in that case hair growth is delayed by the destruction of hair producing structures at the dermal papilla level. In the context of photodepilation, this results in improved efficiency when compared to the delivery of isolated nanocomplexes.

Therefore, an aspect of the present invention relates to a microcomplex for use in photoepilation comprising a nanocomplex which comprise a nanoparticle of a material selected from the group consisting of metals, semiconductors and their mixtures, supporting a Localized Surface Plasmon Resonance, which is coated by forming at least a bond, coordinate or covalent, with at least a polycationic polymer or a heterobifunctional compound which comprises at least a thiol group on one end of the molecule and at least a positively charged functional group on the other end; adsorbed on the surface of a host particle with a diameter comprised between 100 nm and 2000 nm; the microcomplex have a positive Z potential higher than 10 mV.

Another aspect of the invention relates to a process for the preparation of the microcomplex for use in photoepilation as defined above, which comprises the following steps:

a) adding a suspension of nanoparticle coated with at least a polycationic polymer to a host microparticle with a diameter comprises between 100 nm and 2000 nm, under ultrasounds to obtain a microcomplex, and b) separating the microcomplexes obtained in the step a).

The separating step is carried out either by sedimentation, ultrafiltration or any other separation technique Other process for the preparation of the microcomplex comprises the steps of:

a) mixing amino modified host microspheres with a diameter comprises between 100 nm and 2000 nm with a surfactant coated nanoparticles, b) sonicating the suspension obtained in the step a) of the present process, c) incubating under stirring to obtain a microcomplex, and d) coating the resulting microcomplex with a polycationic polymer.

Also the invention relates to a composition that comprises the microcomplexes of the invention which are able to penetrate, upon application on the skin surface, into the hair follicle and stick to the hair cuticle and/or the basal cells near the hair root where they accumulate.

Prior to application of the method, skin and hair follicles can be pretreated to increase the delivery of the microcomplex of the invention to a target region. In some embodiments, hair shafts are cut or removed via shaving, waxing or other techniques to remove hair. In some embodiments pre-treatment with surface exfoliation including mechanical exfoliation and chemical exfoliation removes plugs from the orifice of follicles to increase the targeting of microcomplexes to target region within the hair follicle. Also a preteatment with hot water or steam can be useful to open the hair follicle.

Thus another aspect refers to a photoepilation method which comprises the steps of (i) applying to the skin surface the composition for topical application as defined above, and (ii) applying a radiation to said surface of the skin.

The radiation used in the step (ii) can be from any light source whose emission presents a spectral overlap with the LSP resonance of the nanocomplex comprised in said composition. Examples of light sources are those conventionally used in photoepilation methods, such as Intense Pulsed Light (IPL) or continuous wave and pulsed laser light. Other source of light as Light Emitting devices (LED) is also considered.

Finally, another aspect of the present invention relates to the use of microcomplexes of the invention in a photoepilation method.

BRIEF DESCRIPTION OF THE DRAWINGS

FIG. 4A Untreated hairs, FIG.4B Silica gold microcomplexe, FIG. 4C gold nanocomplexes.

DETAILED DESCRIPTION OF THE INVENTION

Figure 1:
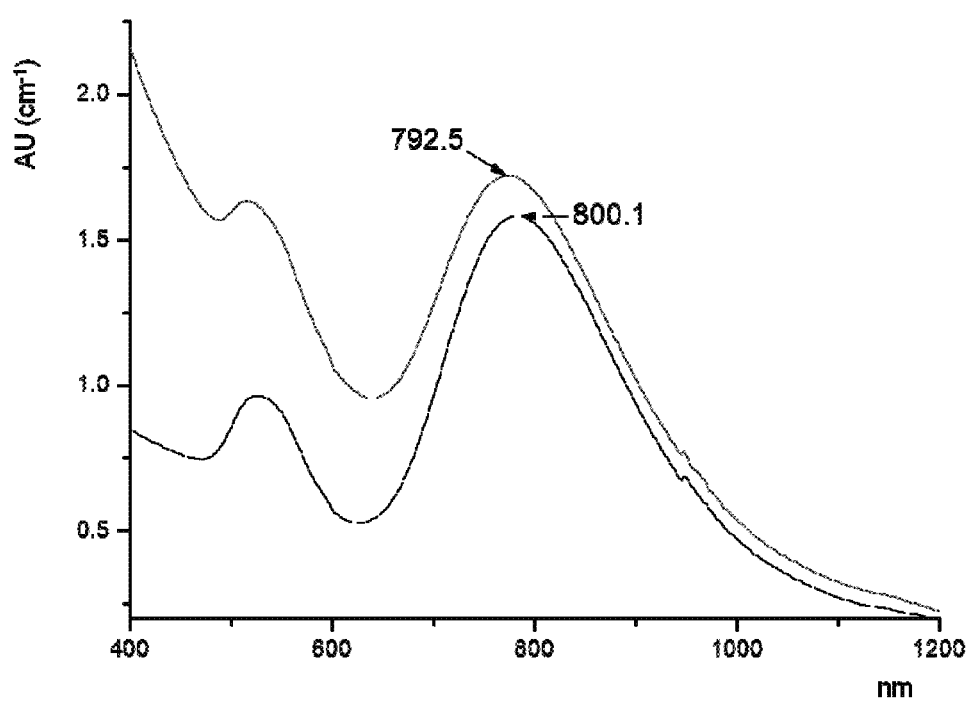
FIG. 1 shows the comparative spectrum of gold nanorods adsorbed (show a peak on 792.5) or not (show a peak on 800.1) onto a silica microparticle surface.

As mentioned above, an aspect of the present invention relates to a microcomplex for use in photoepilation comprising a nanocomplex which comprise a nanoparticle of a material selected from the group consisting of metals, semiconductors and their mixtures, supporting a Localized Surface Plasmon Resonance, which is coated by forming at least a bond, coordinate or covalent, with at least a polycationic polymer or a heterobifunctional compound which comprises at least a thiol group on one end of the molecule and at least a positively charged functional group on the other end; adsorbed on the surface of a host particle with a diameter comprised between 100 nm and 2000 nm; the microcomplex have a positive Z potential higher than 10 mV.

The term "host particle" as used herein refers to particles which are essentially spherical form made of silica, modified silica, cellulose, modified cellulose as for example carboxymethyl cellulose or particles made of polyanionic polymers such as polystyrene sulfonate or polyacrylates. Preferred the host particle is made of silica or activated silica microparticles or surface modified silica microparticles (either with carboxylate, sulfonate, amine groups, epoxy groups or other organic groups). In a particular embodiment the host particle is made of activated silica and in a second particular embodiment the host particle is made of silica modified with amine groups.

In a more preferred embodiment the diameter of the host particle is comprised between 200 nm and 500 nm.

In an embodiment the Z potential is comprised between 10 mV and 150 mV.

In a particular embodiment the metal nanoparticle is a gold nanoparticle.

The nanoparticle presents in the microcomplex of the present invention are designed to present a LSP maximum contained between 650-1200 nm, which is the window where the absorption and thus the photoheating of the biological tissues is minimal. In this way, the contrast of absorption between the microcomplexes and the surrounding tissues is maximized and the possible photothermal damage caused to the surrounding tissues and/or glands is avoided.

A choice of a resonance centered at around 700-900 nm is motivated by the subsequent minimum absorption (photoheating) of biological tissues.

According to a preferred embodiment the microcomplex of the invention presents a localized surface plasmon resonance maximum between 700 and 900 nm.

Furthermore, recent numerical studies enabled to quantify the influence of the geometry of gold NPs on its heating ability. It was demonstrated that the optical field intensity within the metal is the main parameter to be maximized in order to increase the temperature of the NP. This is the reason why, for a given illumination, elongated gold NPs (known as nanorod (NR)) generate more heat than gold nanospheres of the same volume. Considering all above-mentioned parameters, one can design gold NRs to act as efficient punctual heat-sources to be remotely controllable by light. Importantly, the temperature profile associated to a punctual heat source decays in 1/r, where r is the distance from the source.

Therefore according to a preferred embodiment the microcomplex of the invention comprises a gold nanorod.

Hair fibers are strongly keratinized conferring to the hair cuticle high polyanionic, therefore in a preferred embodiment the polycationic polymer is a polyamine or polyimine containing polymer; in a more preferred embodiment the polycationic polymer is quaternary ammonium polymer such as the polyquaternium-n series polymers, polyallyl ammonium polymers and copolymers thereof with polyamines, polyglycosamines and/or polyimines as polyethyleneimine. Among these polymers Chitosan (poly-glucosamine) and polyethyleneimine are polycationic polymers having strong affinity to gold by the formation of multiple weak covalent/coordination bonds leading to strongly charged polycationic (positively charges) nanoparticles. Therefore in a particular embodiment the polycationic polymer is chitosan or polyethyleneimine.

In another embodiment of the invention a heterobifunctional compound is used. The heterobifunctional compound refers to a compound that comprises at least a thiol group on one end of the molecule and at least a positively charged functional group on the other end. Among these compounds Self Assembling Monolayer forming compounds are preferentially used. These compounds from the groups mercapto-(alkyl)-amino/dimethyl amino/quaternary ammonium:

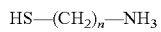

$HS-(CH_2)_n-NH_3$

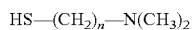

$HS-(CH_2)_n-N(CH_3)_2$

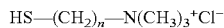

$HS-(CH_2)_n-N(CH_3)_3{}^+Cl^-$

In another embodiment of the invention the chain $-(CH_2)_n-$ can be replaced by a polyoxy-ethylene chain with the general formula: $-(CH_2-CH_2-O)_n-$, using then the series of heterobifunctional polyethylene glycols to obtain positively charged surfaces in the nanoparticles.

According to another embodiment of the invention said chemical compound specifically binds through receptor-mediated processes, to a molecule target present on the basal cells of the hair. Examples of said compounds in this case are antibodies, which can be obtained and thereafter chemically modified to be grafted to the NP surface according to well known methods.

In another aspect of the invention the composition of the invention is cosmetically or pharmaceutically acceptable. According to a particular embodiment the composition is an aqueous suspension. The composition may however be also in form of a gel, milk, lotion, ointment or cream. The microcomplexes are present in a cosmetically efficient amount. Under cosmetically efficient amount is to be understood the minimum amount to achieve a photoepilation effect in a photoepilation method. The composition may further contain other cosmetically or pharmaceutically acceptable ingredients such as solvent or cosmetic additives or vehicles.

Another aspect refers to a photoepilation method which comprises the steps of (i) applying to the skin surface the composition for topical application as defined above, and (ii) applying a radiation to said surface of the skin. According to a particular embodiment the light source is an IPL with a light delivered through a head piece window defining a set area of illumination (emitting between 600-1000 nm). In this case, according to another particular embodiment a higher absorption contrast is achieved by filtering out the emission that does not overlap with the Plasmon resonance, minimizing melanin absorption and thus tissue heating without contributing to hair damage.

The light source can also be a laser device emitting in a wavelength which match with the maximum absorption of the microcomplexes LSP, and in a range between 700-1100 nm. Another aspect refers to the possibility offered by the microcomplexes defined above to decrease the energy necessary to obtain an efficient hair removal. This aspect open the possibility to enlarge the technic to other less powerful light sources as LEDs (Light Emitting Devices). According to a particular embodiment the light source is a LED emitting in a wavelength that matches the maximum of absorption of the microcomplexes and particularly in the range from 700 nm to 1100 nm.

The possibility offered of using lower energy emitting devices also permits to use larger application surfaces which would result in time reduced treatment sessions.

EXAMPLES

The following examples are provided for illustrative means, and are not meant to be limiting of the present invention.

Example 1

Synthesis of the Microcomplexes of the Invention

Preparation of the Microcomplexes

Chitosan covered gold nanorods presenting a surface plasmon resonance (SPR) absorption maximum around 800 nm were prepared as described in the patent application WO2013079105 and maintained in lactate buffer 5 mM pH 6. The nanoparticle suspension presented an absorption maximum of around 6 UA corresponding to 0.2 mg/mL of gold. 10 mL of the nanorod suspension were added of 2.5 mg of silica ($SiO_2$) microparticles of 0.235 micrometers under ultrasounds. The resulting suspension was then kept at room temperature and the formed microcomplexes decanted. Excess nanoparticles were removed and the microcomplexes washed twice with 5 mM lactate buffer pH 6.

The FIG. 1 compares the absorption spectra of the microcomplexes and the dispersed gold nanocomplexes, indicating that absorption properties remain almost unchanged.

Figure 2:
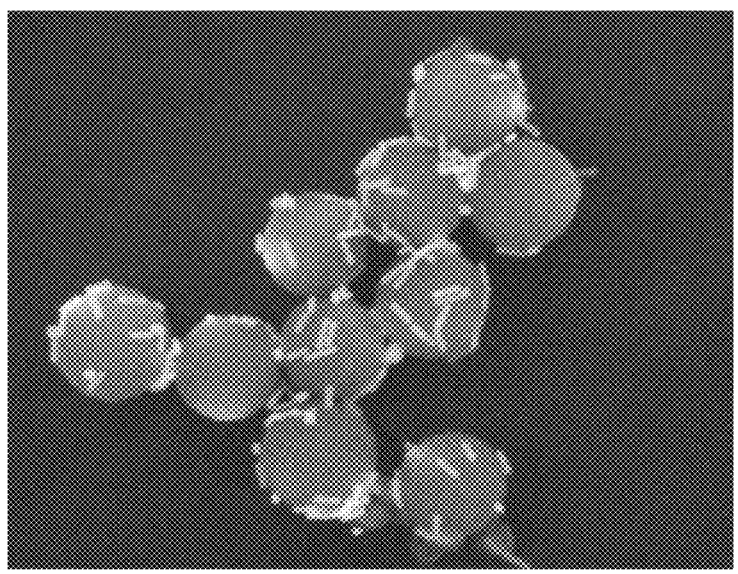
FIG. 2 shows the scanning electron microscopy (SEM) of gold nanorods adsorbed onto a silica microparticle surface.

The FIG. 2 shows a SEM micrography showing that the nanocomplexes accumulate at the microparticles surface.

Example 2

Comparative Example, Nanocomplex Versus Microcomplexes

Nanocomplexes versus microcomplexes: delivery to the hair

Fairs hairs isolated from pork skin and containing the whole root were incubated during 5 minutes in two suspensions of gold-chitosan nanocomplexes and silica-gold-chitosan microcomplexes. The characteristics of the two suspensions were as follows: gold nanorods covered in surface with chitosan presenting and absorption maximum at 800 nm of about 7 UA; gold nanorods covered in surface with chitosan and then adsorbed in the surface of 235 nm silica microparticles and presenting and absorption maximum around 800 nm of about 6 UA.

Figure 3A:
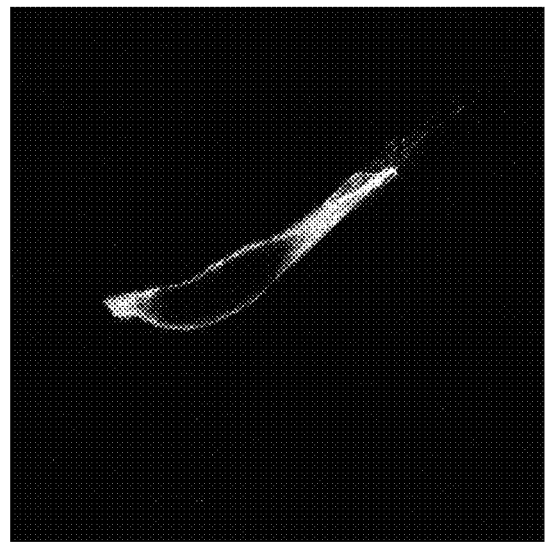
FIG. 3A shows the Two Photon Luminescence (TPL) image of a hair root incubated with gold-chitosan nanocomplexes.
Figure 3B:
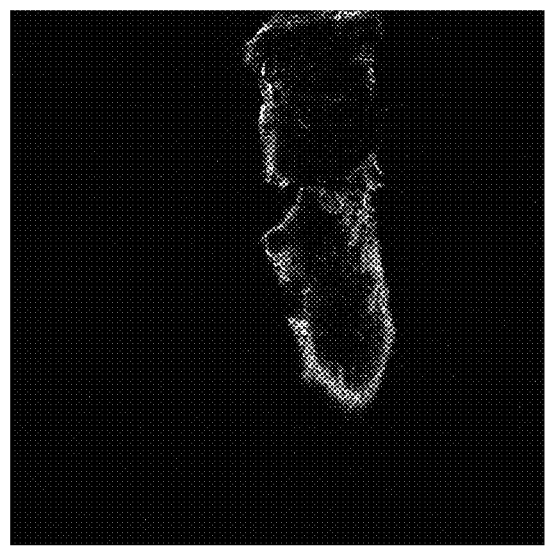
FIG. 3B shows an image of a hair root incubated with silica-gold-chitosan macrocomplexes.

Hairs were incubated at room temperature during 5 minutes and then washed extensively with water. The FIG. 3A and the FIG. 3B show a TPL image of two hairs after incubation with each of the two suspensions showing strong interaction of both nano and microcomplexes with the hair root.

Nanocomplexes Versus Microcomplexes: Photothermal Efficiency

The incubated hair samples were placed on microscopy slides before being illuminated with IPL. Exposure was performed with a single 30 millisec pulse of 4 different energies (3, 5, 7 and 9 joules/cm$^2$). Using a high pass filter at 755 nm the light wavelength range was limited to 755-1200 nm in order to reduce the contribution of melanin to heating.

Damage to the hair root was estimated visually by the change in colour and shape induced by IPL exposure (5 hairs per treated slide).

Figure 4A:
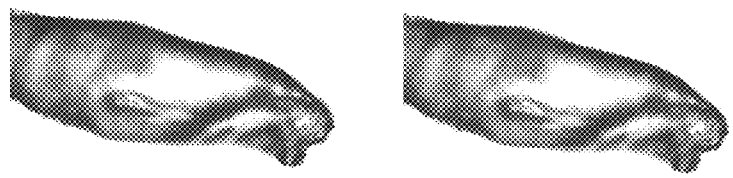
FIG. 4A, 4B. 4C show an illustrative example of the damage observed at 9 joul/cm$^2$.
Figure 4B:
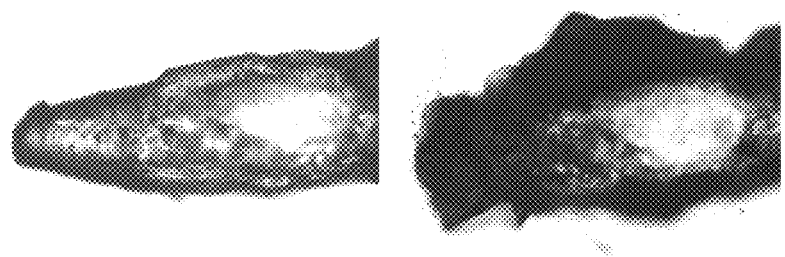
Figure 4C:
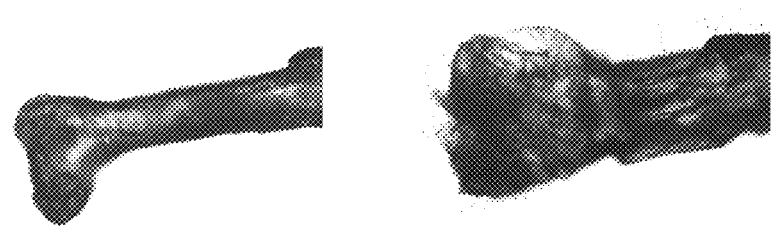

The FIG. 4 A shows that at 9 joul/cm$^2$ no effect is observed on gold complex untreated hairs while the hair root is destroyed either for nanocomplexes (FIG. 4C) or microcomplexes (FIG. 4B).

Figure 5:
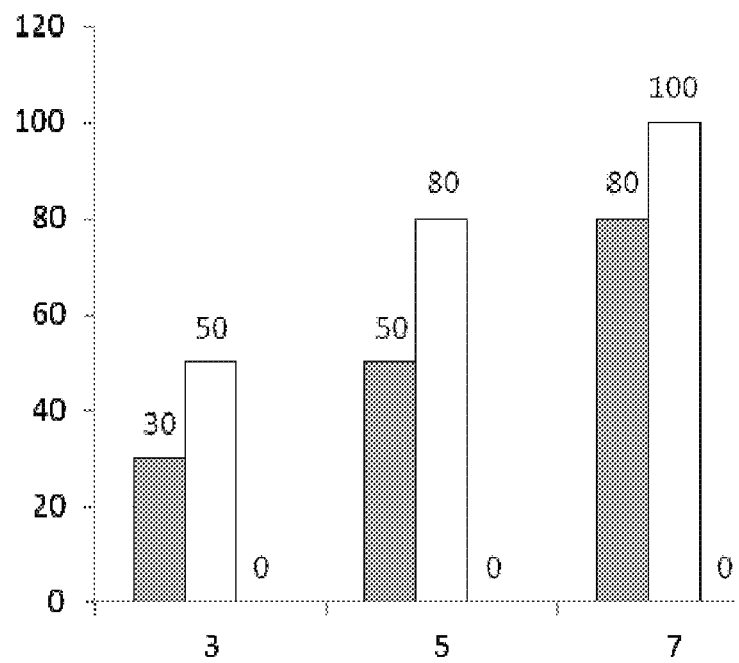
FIG. 5 shows an estimation of the average damage observed for each treatment. Gold untreated hairs (black), gold chitosan nanocomplexes (grey) and silica-gold-chitosan macrocomplexes (white) at 3 J/cm$^2$, 5 J/cm$^2$, 7 J/cm$^2$ and 9 J/cm$^2$.

The FIG. 5 shows comparative effect of IPL on fair hairs for gold untreated hairs, gold chitosan nanocomplexes and silica-gold-chitosan macrocomplexes. IPL consisted on a 30 msec single shot on isolated hairs placed in a microscopy slide. From FIG. 5, we observed a substantial increase of the heating efficiency of silica-gold microcomplexes over nanocomplexes, especially for low fluences.

Study of Heating Efficacy as a Function of the Host Microparticle Particle Size

Three sizes of microcomplexes were prepared by incubating silica microparticles with chitosan covered nanorods as described in Example 1.

In this experiment three sizes of silica microparticles were used (0.235 µm, 0.519 µm and 2 µm). Isolated pork fair hairs were incubated 5 minutes in each microcomplex suspension and then treated with IPL filtered at 755 nm at different energy levels.

Figure 6:
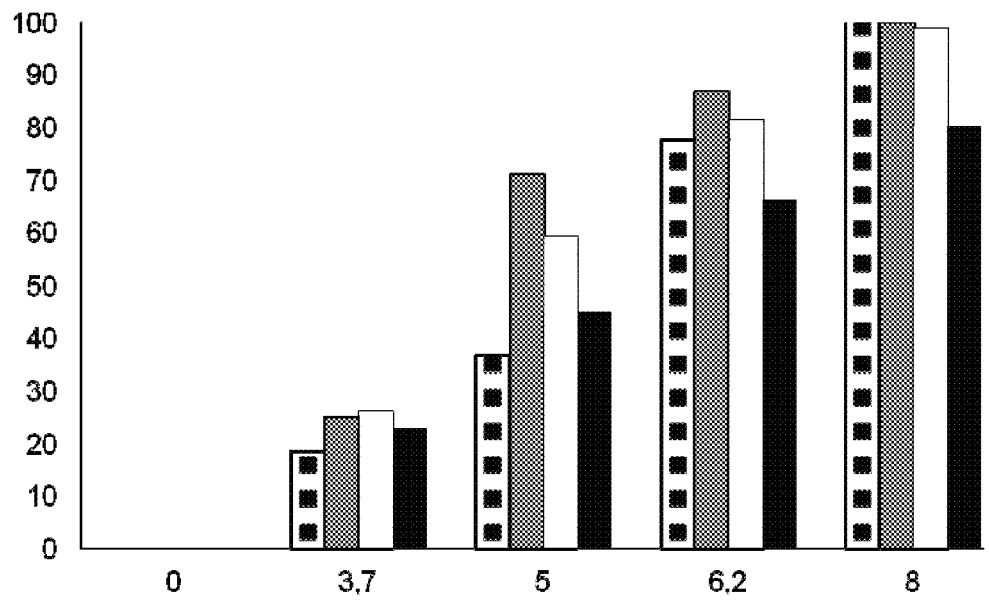
FIG. 6 shows a representation of the relative hair root damage at different energies (abcisas, J/cm$^2$) for different sizes of the host microparticle (nanocomplex (black square, and different silica microparticle of 235 (grey), 519 (white) and 2000 nm (black) diameter respectively).

The amount of damaged to hairs root was estimated by evaluation in changes in shape and color of the hairs using a computer assisted image analysis software. Results are presented in FIG. 6. From these results an optimum size of the microcomplex to effectively transfer heat to the hair root is found to be around 200-500 nm.

Figure 7:
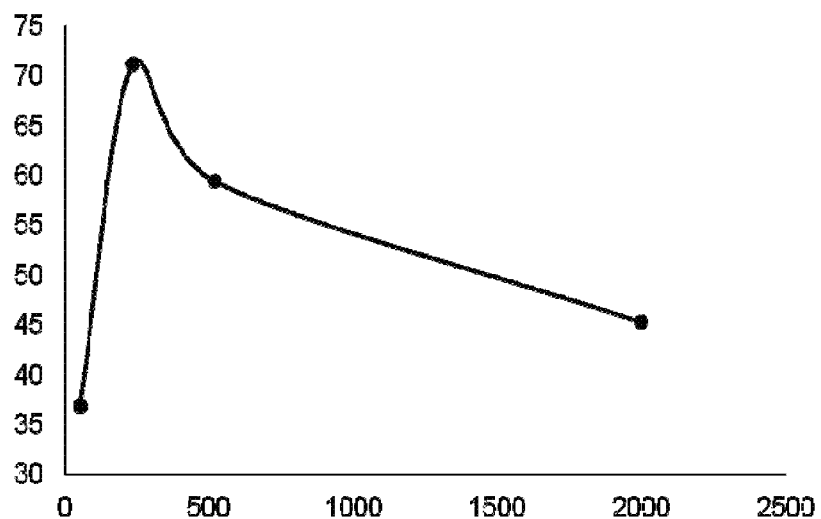
FIG. 7 shows a comparison of the hair root damage at 5 J/cm$^2$ as a function of the host microparticle diameter in nm.

FIG. 7 shows an optimum host micropaticle size around 250 nm, which is more noticeable at 5 J/cm$^2$.

Example 3

Preparation of Microcomplexes of Gold Nanorods on Aminated Silica Microparticles Gold nanorods presenting a maximum SPR are prepared as described in the Example 1. The nanorods suspension is centrifuged and the resulting pellet is re-suspended adjusting the CTAB (Cetyl Trimethyl Ammonium Bromide) concentration to 5 mM.

8 ml of the nanorods suspension are mixed with 2 ml of ethanol and 200 microliters of a silica-aminated microparticles of 237 nm diameter suspension at 50 mg/ml. The resulting suspension is sonicated at 45° C. during 15 minutes, incubated at 45° C. during 2 hours and then left to stand overnight at 30° C. under gentle stirring.

Excess of nanorods are eliminated by decantation and the resulting microcomplexes are washed extensively with pure water.

The resulting microcomplexes are then suspended in a solution of chitosan at 0.5 mg/ml and left stand overnight under gentle stirring at 30° C. This step is devoted to eliminate any CTAB left on the microcomplexes and to passivate the exposed surface of the nanorods linked with a polyaminated polymer.

The microcomplexes resulting are finally washed extensively with pure water.

Example 4

Adsorption of Silica-amino Nanorods Microcomplexes to Hair Roots

Fair pork hairs were incubated 10 minutes in an aqueous suspension of the silica aminated-nanorod microcomplexes (0.5 mg/ml) described in the Example 3.

After this period hairs were washed with water and placed in microscope slides to observe the adsorption of microcomplexes at the keratinized hair root by Two Photon Luminescence (TPL), which is specific of the nanorods structure.

Figure 8:
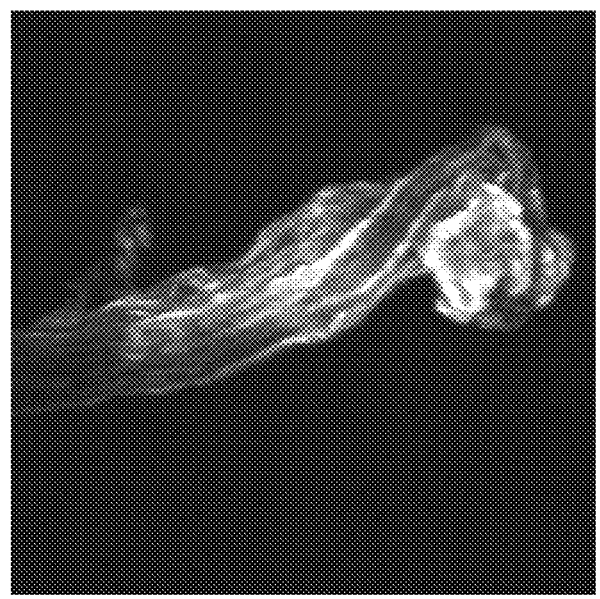
FIG. 8 shows TPL image of a hair root incubated with silica aminated nanorods microcomplexes.

FIG. 8 shows an image of a hair root on which the microcomplexes are effectively adsorbed.

The invention claimed is:

1. A microcomplex for use in photoepilation comprising:
    a nanocomplex which comprise a nanoparticle of a material selected from the group consisting of metals, semiconductors and their mixtures, supporting a Localized Surface Plasmon Resonance, which is coated by forming at least a bond, coordinate or covalent, with at least a polycationic polymer or a heterobifunctional compound which comprises at least a thiol group on one end of the molecule and at least a positively charged functional group on the other end; adsorbed on the surface of a host particle with a diameter comprised between 100 nm and 2000 nm; the microcomplex have a Z potential higher than 10 my.

2. The microcomplex according to claim 1 wherein the diameter of the host particle is comprised between 200 nm and 500 nm.

3. The microcomplex according to claim 2 wherein the host particle is silica.

4. The microcomplex according to claim 3 wherein the silica is a modified silica with amines group.

5. The microcomplex according to claim 1, wherein the microcomplex presents a localized surface plasmon resonance maximum between 700 and 900 nm.

6. The microcomplex according to claim 1, wherein the nanoparticle is a gold nanorod.

7. The microcomplex according to claim 1, wherein the polycationic polymer is a polyamine or polyimine containing polymer.

8. The microcomplex according to claim 7 wherein the polycationic polymer is chitosan or polyethyleneimine.

9. A process for the preparation of the microcomplex according to claim 1, which comprises:
    a) adding a suspension of nanoparticle coated with at least a polycationic polymer to a host microparticle with a diameter comprises between 100 nm and 2000 nm, under ultrasounds to obtain microcomplexes, and
    b) separating the microcomplexes obtained in the step a).

10. A process for the preparation of the microcomplex according to claim 1, which comprises:
    a) mixing amino modified host microspheres with a diameter comprises between 100 nm and 2000 nm with a surfactant coated nanoparticles to produce a suspension,
    b) sonicating the suspension
    c) incubating under stirring to obtain a microcomplex, and
    d) coating the resulting microcomplex with a polycationic polymer.

11. A composition comprising the microcomplex as defined in claim 1.

12. Photoepilation method which comprises the steps of (i) applying to the skin surface the composition for topical application as defined in claim 11, and (ii) applying a radiation from a radiation source to said surface of the skin.

13. Photoepilation method as described in claim 12 on which the radiation source is a LED device emitting in a wavelength ranging from 700 to 1200 nm.

* * * * *